United States Patent [19]

Flint

[11] Patent Number: 5,102,658

[45] Date of Patent: Apr. 7, 1992

[54] ANTIBODY TREATMENT FOR ADIPOSITY

[75] Inventor: David J. Flint, Troon, Scotland

[73] Assignee: National Research Development Corporation, England

[21] Appl. No.: 757,069

[22] Filed: Jul. 19, 1985

[51] Int. Cl.$^5$ ............................................. A61K 35/395
[52] U.S. Cl. ...................... 424/85.8; 514/21;
530/389.1; 530/388.2; 435/240.27
[58] Field of Search ................. 424/85, 85.8; 530/387, 530/909

[56] References Cited

U.S. PATENT DOCUMENTS 4,673,691  6/1987  Bachynsky ........................ 514/567
4,684,623  8/1987  Larrick et al. ....................... 424/85

FOREIGN PATENT DOCUMENTS 70167   1/1983  European Pat. Off. .
80819   6/1969  Luxembourg .
8100514 3/1981  PCT Int'l Appl. ................. 424/361

OTHER PUBLICATIONS

Pillion et al., J. Biol. Chem., 255(19), 9168-76, (1980).
Pillion et al., Chem. Abs., 104:11359, (1985).
Pillion et al., Chem. Abs. 101:704625c, (1984).
McLaughlin et al., Chem. Abs. 102:179547h, (1985).
D. J. Pillion, Chemical Abstracts 99, 137894h (1983).
D. J. Pillion et al., J. Biol. Chem. 253, 3761-3764 (1978).
D. J. Pillion et al., J. Biol. Chem. 254, 3211-3220 (1979).
J. C. Beachy et al., Biological Abstracts 72, 2993 (1981).
M. Afong et al., Can. J. Biochem. Cell. Biol. 63, 96-101 (1985).
A. C. Newby et al., Biochem. J. 146, 625-633 (1975).
A. Cryer et al., J. Develop. Physiol. 6, 159-176 (1984).
H. Coggrave et al., J. Endocrinology, 102 (Supplement), Abstract No. 41 (1984).
C. E. Futter et al., poster P4 exhibited at University of Nottingham 43rd Easter School, Sutton Bonington, Apr. 15-18, 1985.
A. P. Moloney and P. Allen, Proceedings of the Nutrition Society, Jul. 1988 meeting, p. 14.
"Principles of Biochemistry", by A. White, P. Handler, E. L. Smith R., L. Hill and I. R. Lehman, 6th edition. McGraw-Hill Kogakusha Ltd., (1978), pp. 301, 303-304, 572-575.

Primary Examiner—Esther L. Kepplinger
Assistant Examiner—Jeff Kushan
Attorney, Agent, or Firm—Rosenman & Colin

[57] ABSTRACT

A method of preventing controlling or reducing adiposity in which an animal or human being is treated with an effective amount of an antibody to an adipocyte present respectively in said animal or human being.

3 Claims, No Drawings

ANTIBODY TREATMENT FOR ADIPOSITY

This invention relates to the prevention, reduction and control of adiposity in non-human and human animals.

Hitherto the carcass quality in livestock has been manipulated by the administration of steroidal compounds in the form for example of implants. Such compounds are, however, liable to give rise to various difficulties. Undesirable side effects may, for example, be produced in the animals and behaviour may also be adversely affected, because for example, of alteration in the balance of male and female hormones. Further, steroid residues may remain in the carcass and enter the consumer.

It is now been found that adiposity can be controlled, reduced or prevented without such disadvantages.

Accordingly, the present invention comprises a method of preventing controlling or reducing adiposity in which an non-human or human animal is treated with an effective amount of an antibody to an adipocyte present respectively in said animal.

The present invention further includes within its scope an adipocyte antibody per se.

Adipocyte antibodies may be raised by immunisation of a suitable serum donor species which is usually far removed evolutionally from the non-human or human animal to be treated using adipocyte plasma membrane material as antigen.

Accordingly the present invention also includes within its scope a method of producing antibodies to adipocytes which comprises immunising a serum donor with antigenic adipocyte plasma membrane material.

Adipocyte antibodies may be produced alternatively from cultured hybridomas of myeloma cells and lymphocytes secreting the antibodies. The lymphocytes are suitably derived from the spleens of mammals e.g. mice or rats immunised with adipocyte plasma membranes.

In accordance with a further aspect of the present invention, a method of producing an antibody to an adipocyte comprises culturing a hybridoma of a myeloma cell and a lymphocyte capable of secreting the antibody.

The present invention further includes within its scope such a hybridoma per se.

It will be appreciated that the culture of hybridomas permits the production of antibodies on a large scale without recourse to antiserum donors.

Antigenic adipocyte material is usually derived from the same species, and preferably the same strain, as the animal to be treated with antibodies. In the case of human treatment, the antigenic material may be derived from the individual to be treated, because in this way the antibody is highly specific and can be provided in relatively low effective doses with minimal risk of side effects. The antigenic material may be derived from a single fat depot e.g. a parametrial subcutaneous or perirenal depot or a plurality of depots. When the treatment of human adiposity is concerned, abdominal or subcutaneous fat cells may be chosen as antigenic material.

Fat cells which are solely white or both white and brown fat cells may provide the source of antigenic material. In the latter case, although treatment of an animal with brown fat cell antibodies lyses the cells and thus reduces thermogenesis the intake of food may thereby be reduced with a cost saving advantage because there is concomitant control of fat deposition by administration of antibodies against white adipocytes.

Typically, fat tissue is treated, e.g. with a collagenase, to yield isolated adipocytes therefrom which are lysed to liberate adipocyte plasma membrane material, the material being purified before administration to an antibody donor.

It will be appreciated that when antibodies are derived directly from an antiserum, the donor is preferably a relatively large animal differing, as hereinbefore described, evolutionally from the antigen donor.

Antigenic material is usually administered to an antiserum donor with an adjuvant which heightens the immune response for example incomplete Freund's adjuvant. The whole antiserum may sometimes be used in the treatment of the non-human or human animal although it is generally preferable to purify antibodies from, for example, serum albumins e.g. by precipitation of antibodies from antiserum which is usually followed by concentration thereof.

Treatment of human or non-human animals is usually carried out by injection of antibodies intraperitoneally or intravascularly. Although dosage levels and intervals can be established by simple trials, it is believed that levels within range 1 nanogram antibody/kg body weight to 320 mg/kg body weight will be found satisfactory, 25–100 mg/kg body weight being typical. The interval between treatments will usually be no less than 24 hours and may reach several years, particularly in the case of human adiposity.

Applications of the present invention include:

The immumisation of lambs to produce lean meat; the production of lean ewes, for example in lowland farming where excess fatness may be unnecessary and energetically expensive; the production of low fat milk from lean cattle fed with concentrates; the reduction of excess abdominal fat in broiler chickens and in laying hens (which carry considerable fat as they age and have costly nutritional requirements); reduction of fat and particularly subcutaneous fat in duck; the production of leaner carcasses in pigs and the reduction of reproduction problems due to obesity; the reduction of human obesity.

The invention is illustrated by the following Example:

EXAMPLE

A. Preparation of rat fat cell membranes for immunization

Parametrial, perirenal and subcutaneous adipose tissue was removed from 180–250 g female Wistar rats. The tissue was minced with scissors and incubated for 90 min at 37° C. in Krebs ringer phosphate buffer containing 1 mg/ml collagenase and 3 mg/ml bovine serum albumin to prepare isolated adipocytes. The digested tissue was filtered through a nylon sieve and the isolated adipocytes washed by flotation 3x in Krebs ringer phosphate.

The washed cells were then vortexed for 60 seconds in 100 mM Tris HCl buffer containing 0.25M sucrose and 20 mM EGTA ethylene glycol-bis ($\beta$-aminoethylether)-N,N,N',N'-tetracetic acid to lyse the cells and centrifuged (2000 g×5 min) to remove the lipid. The infranatant containing broken cell debris (including plasma membranes) was centrifuged at 13000 g for 15 min to harvest the membranes. The supernatant was discarded and the pellet resuspended in 2 ml medium, homogenised and then mixed with a Percoll-containing density gradient (Tris HCl medium containing Percoll 17.5% (v/V) medium and centrifuged at 5000 g×15 min. The purified plasma membranes appeared at the top of the gradient and were carefully removed and harvested by centrifugation at 80000 g for 20 min. The pellet was finally resuspended in Tris HCl buffer pH 7.4, containing 0.15M NaCl, and used for immunization.

B. Immunization of sheep with rat fat cell membranes 2-year old Clun sheep were injected subcutaneously with 6 ml of incomplete Freund's adjuvant (2 parts oil to 1 part aqueous phase) containing 250 μg of purified rat adipocyte plasma membrane. The injections were repeated at 3-weekly intervals and blood was obtained 10-18 days after the third injection and again 10-18 days after subsequent boosts.

The blood was allowed to clot and then centrifuged at 2000 g for 20 min to obtain serum. A crude immunoglobulin fraction was prepared from the serum by precipitation in 45% $NH_4SO_4$ and centrifugation at 2000 g for 30 min. The immunoglobin-containing pellet was redissolved in 0.1M phosphate buffer pH 7.4 and dialyzed extensively to remove all traces of $NH_4SO_4$. This material was stored at $-20°$ C. until used for injection into rats.

C. In vivo treatment of rats with anti-rat-adipocyte serum

Female Wistar rats weighing 100-130 g were injected intraperitoneally with 2 ml equivalent of anti-rat-adipocyte serum daily for 4 days. Food and water intakes were recorded and animals were killed 7 days, 3 and 8 weeks after the beginning of treatment. Parametrial, perirenal and subcutaneous fat depots were removed, weighed and isolated adipocytes prepared by collagenase digestion in order to determine the number and size of fat cells. Liver, kidneys, spleen and gut were also removed and weighed and portions fixed in 5% glutaraldehyde for histological examination. 5 μm sections were cut and stained with haematoxylin and eosin. The remainder of the carcass was freeze-dried to determine total body water, ether-extracted to determine remaining body fat and the carcass was finally ground to a fine powder to enable total body nitrogen (protein) to be determined by Kjeldahl analysis.

The results are shown in the Table under three headings: Parametrial, Subcutaneous and Peri-renal relating to the type of fat depot affected by treatment.

In the Table p is a measure of confidence in a given result pl represents: picoliter units

TABLE

| | Time from treatment | Parametrial | | | Subcutaneous | | | Peri-renal | | |
|---|---|---|---|---|---|---|---|---|---|---|
| | | Dry weight g | Mean cell volume pl | cell number × $10^{-6}$ | Dry weight g | MCV pl | cell number g | Dry weight g | MCV pl | cell number × $10^{-6}$ |
| Anti-serum treated | 8 days | 0.55⁻⁻⁻ ±0.06 | 41 ±3.21 | 14.9⁻⁻⁻ ±1.38 | 1.20⁻⁻⁺ ±0.16 | 61 ±5.03 | 24.9⁺ ±2.65 | 0.46⁺⁺⁺ ±0.03 | 77 ±11.80 | 6.3⁺ ±0.58 |
| | 3 weeks | 1.22⁻⁻⁻ ±0.20 | 77 ±8.09 | 17.8⁻⁻ ±3.13 | 1.68⁻ ±0.23 | 84 ±18.76 | 29.9 ±8.71 | 1.32⁺⁺⁺ ±0.15 | 116⁺⁺⁺ ±10.09 | 12.8 ±0.8 |
| | 8 weeks | 2.36⁻⁻⁻ ±0.44 | 166⁻⁻ ±28.68 | 15.5⁻⁻⁻ ±0.38 | 3.30⁺ ±0.46 | 126 ±22.59 | 31.7 ±4.86 | 3.00 ±0.54 | 230 ±68.05 | 15.2 ±2.03 |
| Control | 8 days | 1.24⁻⁻⁻ ±0.11 | 48 ±2.80 | 29.4⁻⁺⁺ ±3.06 | 2.20⁺⁺⁺ ±0.87 | 70 ±7.81 | 36.9⁻ ±4.32 | 0.75⁻⁺⁺ ±0.04 | 88 ±8.78 | 9.9⁺ ±1.14 |
| | 3 weeks | 3.69⁻⁺⁺ ±0.49 | 104 ±16.20 | 41.7⁻⁻ ±4.96 | 2.99⁺ ±0.29 | 115 ±8.78 | 32.6 ±5.36 | 2.3⁺⁺⁺ ±0.225 | 178⁺⁺⁺ ±0.98 | 14.7 ±1.04 |
| | 8 weeks | 8.23 ±0.77 | 330 ±17.27 | 27.45 ±2.23 | 4.83 ±0.35 | 173 ±16.38 | 32.3 ±4.06 | 4.07 ±0.29 | 360 ±49.31 | 12.9 ±0.9 |

⁻ = p is less than (<) 0.05.
⁻⁻ = p < 0.01.
⁻⁻⁻ = p < 0.001

I claim:

1. A method of treating adiposity in a patient animal, which comprises administering to said patient animal an effective amount of a fat cell-specific antibody to white fat cell tissue of a donor animal, said tissue consisting of plasma membranes, or to an antigenic determinant present in said plasma membranes, and said antibody being effective to reduce the weight and/or number of fat cells present in a fat depot of a patient animal.

2. A method according to claim 1 wherein antiserum of the donor animal is administered.

3. A method according to claim 2 or 1 wherein the patient animal is selected from the group consisting of lambs, cows and pigs.

* * * * *